US009662123B2

(12) United States Patent
Tally et al.

(10) Patent No.: US 9,662,123 B2
(45) Date of Patent: May 30, 2017

(54) VERTICAL CUTTER AND METHOD OF USE

(71) Applicants: William Carlton Tally, Athens, GA (US); Kenneth Richard Barra, Acworth, GA (US)

(72) Inventors: William Carlton Tally, Athens, GA (US); Kenneth Richard Barra, Acworth, GA (US)

(73) Assignee: Amendia, Inc., Marietta, GA (US)

(*) Notice: Subject to any disclaimer, the term of this patent is extended or adjusted under 35 U.S.C. 154(b) by 359 days.

(21) Appl. No.: 14/448,490

(22) Filed: Jul. 31, 2014

(65) Prior Publication Data
US 2016/0030060 A1 Feb. 4, 2016

(51) Int. Cl.
*A61B 17/32* (2006.01)
*A61B 17/16* (2006.01)
*A61F 2/44* (2006.01)
*A61F 2/46* (2006.01)
*A61B 17/00* (2006.01)
*A61B 17/3207* (2006.01)

(52) U.S. Cl.
CPC .. *A61B 17/1671* (2013.01); *A61B 17/320016* (2013.01); *A61F 2/44* (2013.01); *A61F 2/4675* (2013.01); *A61B 17/320708* (2013.01); *A61B 2017/00261* (2013.01); *A61B 2017/00473* (2013.01); *A61B 2017/00867* (2013.01); *A61B 2017/320008* (2013.01)

(58) Field of Classification Search
CPC ........ A61B 17/1671; A61B 17/320708; A61B 17/320725; A61B 17/320783; A61B 2017/320791
See application file for complete search history.

(56) References Cited

U.S. PATENT DOCUMENTS

| | | | | |
|---|---|---|---|---|
| 752,356 A * | 2/1904 | Pilling | ........... | A61B 17/320708 606/160 |
| 928,011 A * | 7/1909 | Whitlock | ....... | A61B 17/320708 606/160 |
| 1,015,461 A * | 1/1912 | Vlchek | ................... | A47L 13/08 30/169 |
| 2,876,777 A * | 3/1959 | Kees, Jr. | ................ | A61B 17/32 606/84 |
| 3,502,082 A * | 3/1970 | Chatfield | ....... | A61B 17/320708 30/40.1 |
| 4,210,146 A | 7/1980 | Banko | | |
| 4,932,957 A * | 6/1990 | Zwick | ................ | A61B 10/0291 600/570 |

(Continued)

Primary Examiner — David Bates
(74) Attorney, Agent, or Firm — David L. King

(57) ABSTRACT

A detachable vertical cutter for insertion into a cylinder or tube is formed as a single unitary structure. The single blade has a pair of tool attachment end portions and a cutting blade extending in a loop between the attachment ends. The cutting blade is inclined vertically relative to a longitudinal axis of a cylinder or tube into which the attachment ends can slide into. The cutting blade has a cutting edge, a portion of which when extended free of the cylinder or tube will extend a distance greater than the tube outside diameter. The cutting edge when pushed inwardly and pulled outwardly between adjacent vertebrae scrapes and cuts disc material. When retracted the cutting blade deflects into the cylinder or tube for insertion or extraction into or from the disc space.

11 Claims, 7 Drawing Sheets

(56) References Cited

U.S. PATENT DOCUMENTS

| | | | |
|---|---|---|---|
| 5,250,061 A * | 10/1993 | Michelson | A61B 17/1671 606/160 |
| 5,697,889 A * | 12/1997 | Slotman | A61B 17/025 600/204 |
| 5,709,697 A * | 1/1998 | Ratcliff | A61B 10/0266 606/167 |
| 5,755,732 A | 5/1998 | Green et al. | |
| 5,904,690 A * | 5/1999 | Middleman | A61B 17/29 606/113 |
| 6,506,151 B2 | 1/2003 | Estes et al. | |
| 6,679,897 B2 * | 1/2004 | Josephson | A61B 17/26 600/570 |
| 6,746,451 B2 | 6/2004 | Middleton et al. | |
| 7,060,073 B2 * | 6/2006 | Frey | A61B 17/1604 606/247 |
| 7,153,303 B2 | 12/2006 | Squires et al. | |
| 7,500,977 B2 | 3/2009 | Assell et al. | |
| 7,530,993 B2 | 5/2009 | Assell et al. | |
| 7,588,574 B2 | 9/2009 | Assell et al. | |
| 7,632,274 B2 | 12/2009 | Assell et al. | |
| 7,914,535 B2 | 3/2011 | Assell et al. | |
| 8,052,613 B2 | 11/2011 | Assell et al. | |
| 8,172,848 B2 | 5/2012 | Tomko et al. | |
| 8,172,853 B2 | 5/2012 | Michelson | |
| 8,221,425 B2 * | 7/2012 | Arcenio | A61B 17/1671 606/79 |
| 8,469,959 B2 | 6/2013 | Jacob et al. | |
| 8,480,675 B2 * | 7/2013 | Betts | A61B 17/1617 606/180 |
| 8,523,866 B2 | 9/2013 | Sidebotham et al. | |
| 9,028,499 B2 * | 5/2015 | Keyak | A61K 51/1279 606/79 |
| 9,226,764 B2 * | 1/2016 | O'Neil | A61B 17/32 |
| 9,332,995 B2 * | 5/2016 | Russo | A61B 17/1635 |
| 2004/0267269 A1 * | 12/2004 | Middleton | A61B 17/1617 606/84 |
| 2006/0116690 A1 * | 6/2006 | Pagano | A61B 17/025 606/93 |
| 2008/0114364 A1 * | 5/2008 | Goldin | A61B 17/1617 606/79 |
| 2008/0249552 A1 * | 10/2008 | Eliachar | A61B 17/320016 606/171 |
| 2011/0184420 A1 | 7/2011 | Barnhouse et al. | |
| 2012/0271313 A1 * | 10/2012 | Lauchner | A61B 17/1671 606/84 |
| 2015/0157357 A1 * | 6/2015 | Bennett | A61B 17/320708 606/131 |

\* cited by examiner

VERTICAL CUTTER AND METHOD OF USE

TECHNICAL FIELD

The present invention relates to an improved tissue and bone surface scraping and cutting device for preparation of the spinal disc space for implantation of a fusion implant device.

BACKGROUND OF THE INVENTION

In open spinal vertebrae surgical procedures, the surgeon makes an incision through the skin and muscle tissue and exposes the area to be worked on using retractors separating the tissue above the adjacent vertebral bodies and the interposed disc. Using cutting devices such as a spoon curette or rongeur, the surgeon cuts away the bone and disc material and prepares a space for a spinal fusion device to be placed.

In minimal invasive surgery, the large incision is not used and in its place a smaller cut is made just large enough to position a small hollow tube or cylinder into the disc space between the two vertebrae to be fused together. It is through this tube that the cutting tools must pass to remove the disc material and prepare the space for a fusion implant device. The vast majority of these cutting devices operate by rotational cutting of the tissue to be removed. This allows for a circular cross sectional removal of the disc, but requires rather difficult angulation to flatten or widen the space being prepared. A secondary issue is to flex into a tube fitting compressed size; the blades typically have two or more separate cutting blades as in U.S. Pat. No. 5,709,697. This enables the blades to deflect into a tube, but uses a small pointy tip prone to break when in use leaving metal fragments.

Very importantly, these rotational devices are limited in vertical reach that can be achieved. In some small patients, this represents little trouble, but in larger boned patients, the vertical space required for the implant can exceed the capacity of the device.

The present invention as described hereinafter avoids these issues in a new and improved way to provide the surgeon a much simpler and efficient way to prepare the disc space for implantation.

SUMMARY OF THE INVENTION

A vertical cutter for insertion into a cylinder or tube is formed as a single unitary structure. The single blade has a pair of tool attachment end portions and a cutting blade extending in a loop between the attachment ends. The cutting blade is inclined vertically relative to a longitudinal axis of a cylinder or tube into which the attachment ends can slide into. The cutting blade has a cutting edge, a portion of which when extended free of the cylinder or tube will extend a distance greater than the tube outside diameter. The cutting edge when pushed inwardly and pulled outwardly between adjacent vertebrae scrapes and cuts disc material. When retracted the cutting blade deflects into the cylinder or tube for insertion or extraction into or from the disc space.

The blade is cut from a flat sheet of shaped memory alloy and heat set to form the loop. The sheet has a nominal thickness of 0.5 mm or greater. The cutting blade has a nominal width of 2.0 mm or greater. The cutting edges are the inclined outer edges at the intersection of the thickness and the width. The cutting blade has curved opposing sides spanning a nominal maximum width between opposite sides a distance of 10.5 mm or greater.

The cutting blade when withdrawn into the tube or cylinder bends or deflects the curved opposing sides of the cutting blade to fit the inside diameter. This also lowers or bends the flattened end vertical inclination to slide into the tube or cylinder. The cutting blade has flattened distal end portion between the two curved sides along a vertical cutting peak extending at least 3 mm. The cutting blade is configured to fit into a tube or cylinder having a nominal outside diameter of 8 mm. The vertical inclination of the cutting blade extends at least 2 mm or greater above the outside diameter of the tube when the cutting blade is extended free of the tube.

A vertical cutting tool has a shaft, a tube or cylinder and a single cutting blade. The shaft has the cutting blade attached at one end and is externally threaded at an opposite end. This hollow tube or cylinder is for receiving the shaft internally. A rotatable knot is affixed to the hollow tube and is rotatable independent of the tube or cylinder. The knob has internal threads to engage the threads of the shaft. This rotatable knob adjusts the protruding amount to deploy the cutting blade. The single vertical cutter has a pair of tool attachment end portions and a cutting blade extending in a loop between the attachment ends. The cutting blade is inclined vertically relative to a longitudinal axis of a cylinder or tube into which the attachment ends slide into. The cutting blade has a cutting edge, a portion of which when extended free of the cylinder or tube extends a distance above the tube outside diameter. The cutting edge when pushed inwardly and pulled outwardly scrapes and cuts the disc material, and when retracted deflects into the cylinder or tube for insertion or extraction into or from the disc space. The vertical cutting tool further comprises a push pull knob fixed to the rotatable knob to cut inwardly and outwardly parallel to the tube or cylinder longitudinal axis.

The vertical cutter of the present invention allows for the method of preparing a void space between adjacent vertebrae for placing a fusion implant device comprises the steps of locating a position on the patient to make an incision; cutting the tissue at the location by making a small incision; placing an outer guide tube having an inside diameter into the incision; inserting a cutting tool with a retracted cutting blade inside a tube sized to pass through the inside diameter of the guide tube while having the cutter stowed internally; extending the tool tube past the guide tube directed toward a disc space; protracting the cutting blade free of the tool tube while orienting the cutting blade vertically up or down relative to a longitudinal axis of the tool tube and wherein the protracted cutting blade has a loop shape with an inclined cutting edge extending several mm above or below the tube; cutting away disc tissue directed at one vertebrae to form a void space by pushing and pulling the tool in an axial direction; scraping the cutting blade along the exposed bone surfaces of the adjacent vertebrae thereby removing an outer layer or layers of bone tissue and laterally inclining the guide tool left or right slightly to widen the void space; turning the tool 180 degrees to repeat the steps of cutting away disc tissue and scraping bone layers of the other vertebra to complete the void space; and retracting the cutting blade and withdrawing the cutting tool.

The method can further include a step of retracting the cutting blade prior to turning the tool 180 degrees. The method wherein the cutting edge has a flat portion extending at least 3 mm above the tool tube and the tool tube has an outside diameter of 8 mm. The method wherein the cutting edge can cut disc tissue and vertebral bone to form a total maximum void space height over 14 mm, 7 mm upwardly and 7 mm downwardly between two adjacent vertebrae. The method wherein the cutting blade can be partially refracted to cut at lower heights.

DEFINITIONS

As used herein and in the claims:

A "curette" is a surgical instrument designed for scraping or debriding biological tissue or debris in a biopsy, excision, or cleaning procedure. In form, the curette is a small hand tool, often similar in shape to a stylus; at the tip of the curette is a small scoop, hook, or gouge.

A "rongeur" is a strongly constructed instrument with a sharp-edged, scoop-shaped tip, used for gouging out bone.

BRIEF DESCRIPTION OF THE DRAWINGS

The invention will be described by way of example and with reference to the accompanying drawings in which.

DETAILED DESCRIPTION OF THE INVENTION

Figure 1:
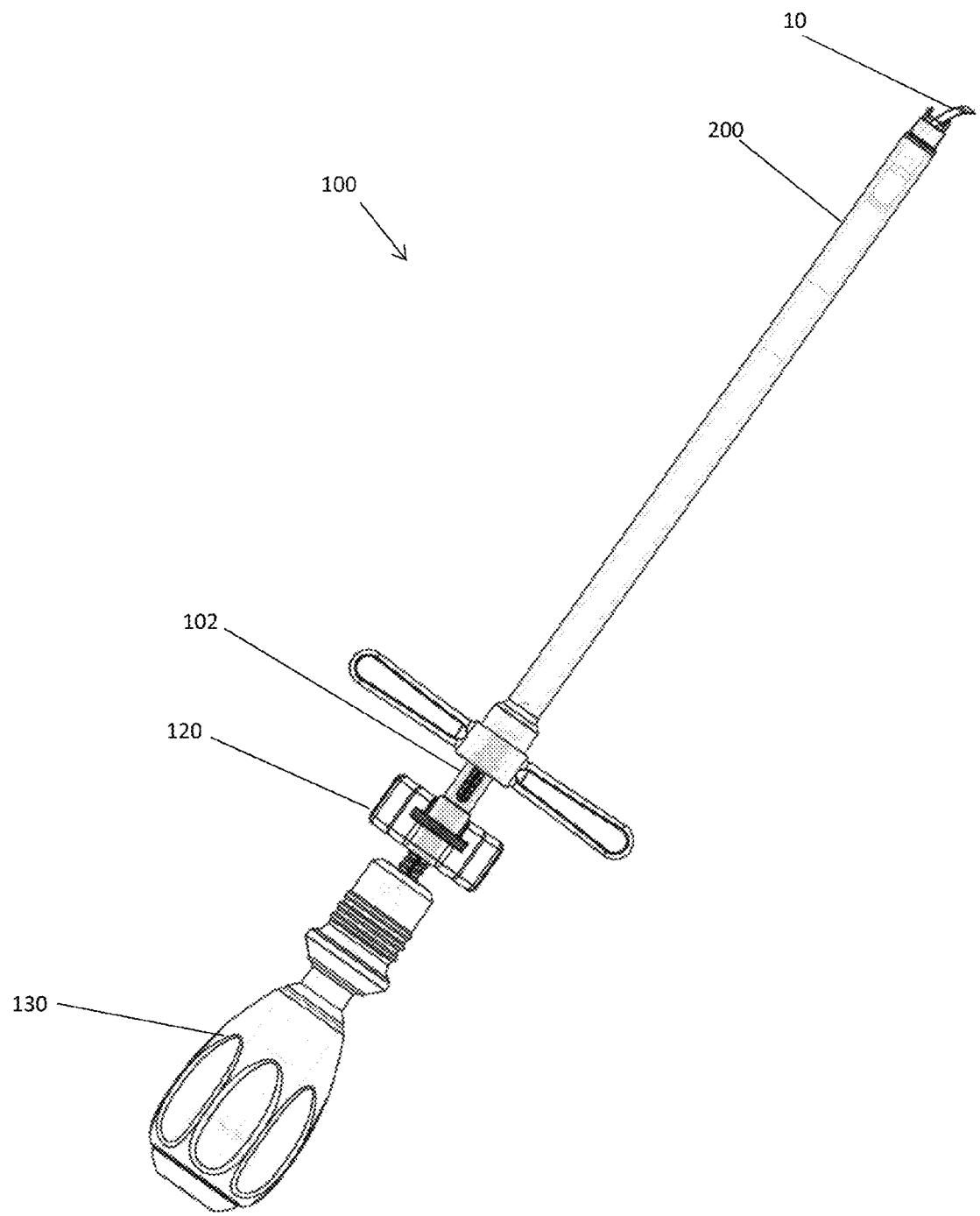
FIG. 1 is a perspective view of the cutter tool assembly of the present invention.
Figure 1A:
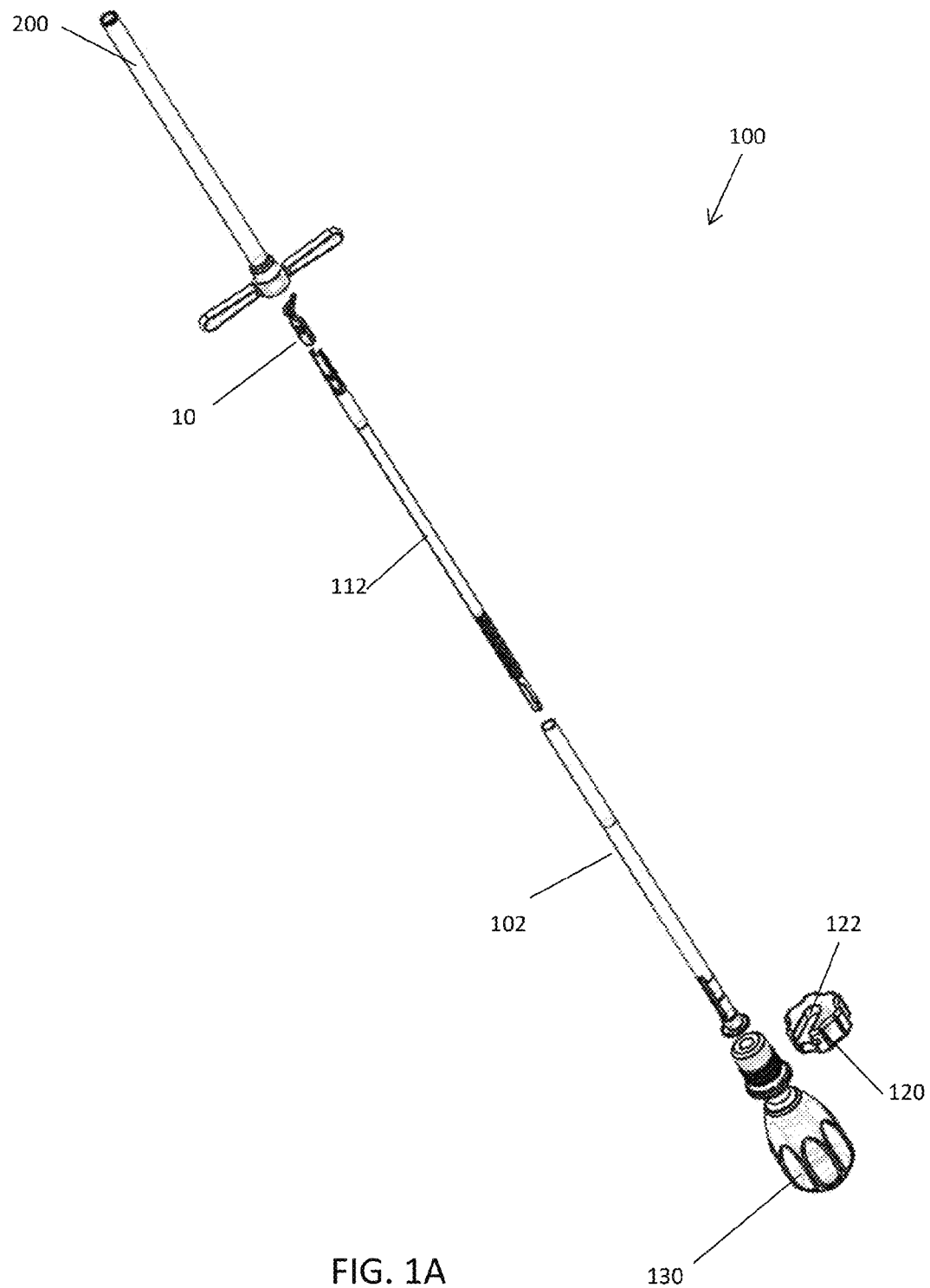
FIG. 1A is an exploded view of the tool assembly of FIG. 1.

With reference to FIGS. 1 and 1A, the cutting tool device 100 of the present invention is illustrated. The device 100 includes a detachable vertical cutter 10, a tool tube 102, a rotatable retraction and protraction knob 120 and a push pull knob 130 to provide linear cutting capability as the tool 100 is pushed and pulled inward between two vertebral bodies to remove disc tissue and to scrape the bone exposed end plate surfaces.

Figure 2A:
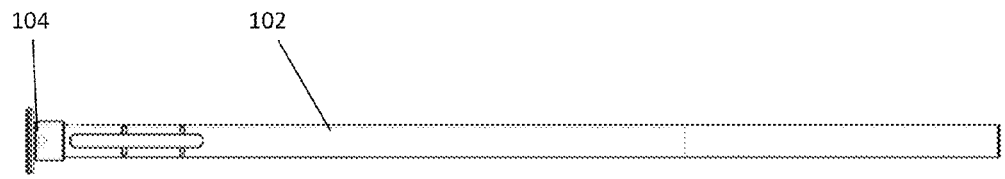
FIG. 2A is a plan view of the tooling tube.
Figure 3:
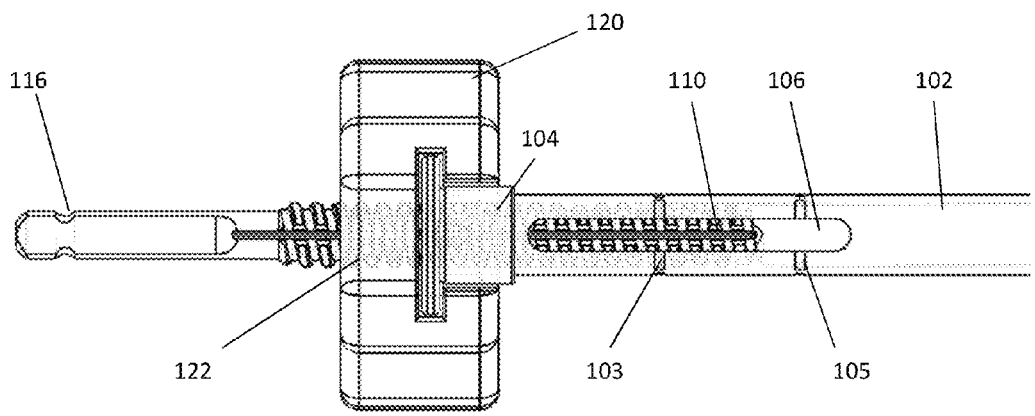
FIG. 3 is a plan side view illustrating the rotatable retraction and protraction knob for moving the cutter blade of the cutting tool into and out of the tooling tube.

With reference to FIG. 1A, further illustrated internal to the tool tube 102 is a shaft 112. The shaft 112 provides a way to attach the vertical cutter 10. As further illustrated in FIG. 2A, the tube 102 has a "T" shaped end 104 that is adapted to fit in the rotatable knob 120 as illustrated in FIG. 3. The "T" shaped end 104 has a knob 120 mounted thereabout so that the knob 120 can rotate without rotating the tube 102.

Figure 2B:
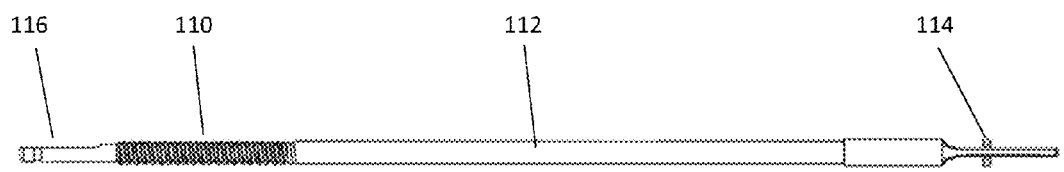
FIG. 2B is side plan view of the internal shaft.

The knob 120 has internal threads 122 adapted to engage the threads 110 of the shaft 112 as illustrated in FIG. 2B. The combination of threads 110, 122 are designed so the shaft can be pulled or pushed axially along the longitudinal axis of the tool by the rotation of the knob 120 best illustrated in FIG. 3. A slot is provided in the tool in FIG. 3 exposing the threads 110 of the shaft 112. The threads 110 can be moved between positions 105 and 103 or further if so desired. This open window 106 provides a means for the surgeon to see the amount of travel that the vertical cutter 10 is making relative to the tool tube 102 when it is positioned inside the vertebral bodies. The shaft 112 has a flat end 116 to which the knob 130 is fixed.

Figure 4:
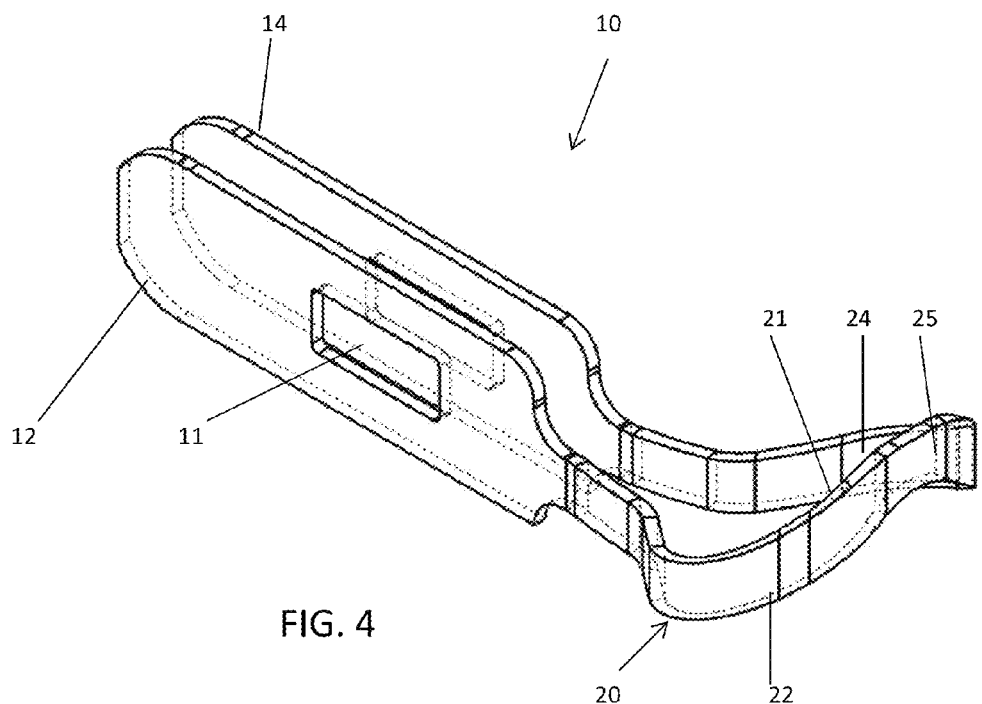
FIG. 4 is a perspective view of the cutting blade of the present invention as formed.
Figure 4A:
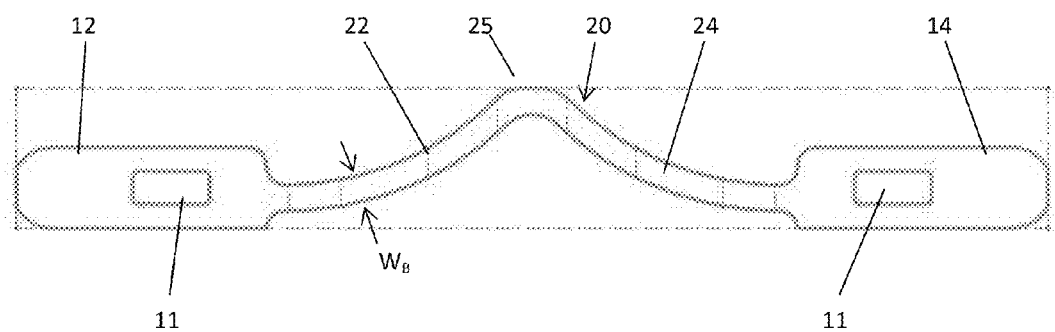
FIG. 4A is a plan view of the cutting blade, the dashed lines representing the sheet from which the cutting blade can be formed.
Figure 4B:
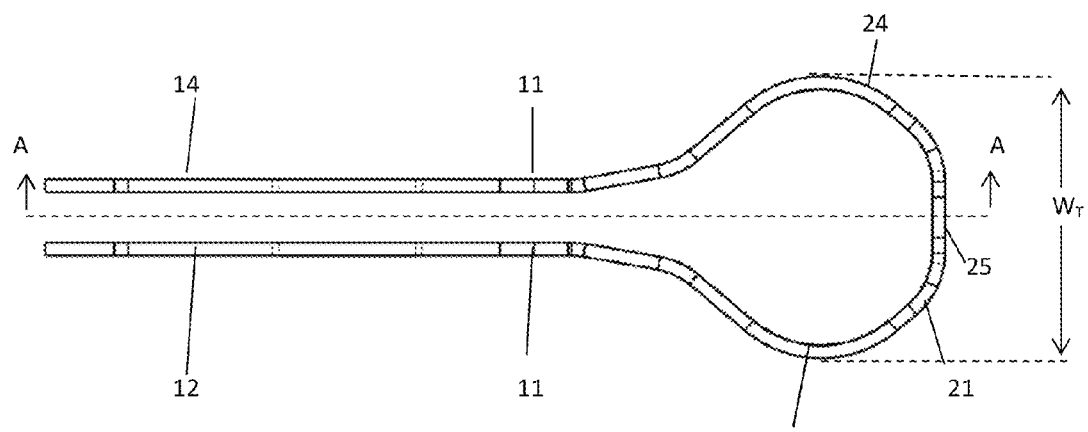
FIG. 4B is a top view of the cutting blade as formed.

With particular reference to the detachable vertical cutter 10, as illustrated in FIGS. 4 through 7, the vertical cutter 10 has attachment ends 12 and 14 with an opening 11 that will conveniently fit on the attachment location 114 of the shaft 112. The openings 11 are oriented at 90 degrees to attachment locations 114. The attachment locations 114 are positioned on each side of the shaft 112 such that when the vertical cutter 10 is mounted on the attachment shaft 112 and pulled inside the tube 102 it securely holds the vertical cutter 10 in position so that it can be pulled internally within the tube 102. As illustrated in FIG. 4A, the vertical cutter 10 was formed as a single piece, preferably of shaped memory alloy material such as Nitinol wherein the material was cut from a blank sheet approximately 0.5 mm thick. The blank sheet is illustrated by dashed lines in FIG. 4A. As shown, the attachment ends 12 and 14 are at the extremes of this sheet where the cutting blade 20 is interposed between the attachment ends 12, 14. As shown, the width $W_B$ is approximately 2 mm in the exemplary embodiment. Punched through the attachment ends 12, 14 are the attachment holes 11 as illustrated. The cutting blade width $W_B$ is substantially uniform across the cutting blade 20, however may be slightly narrower at a flat portion 25. The flat portion 25 extends about 3 mm in length. When the shaped memory alloy material is formed into the desired cutting blade shape which is of a general oval nature as illustrated in the top view of FIG. 4B, the flat portion 25 will be at the very peak of the vertically inclined cutting blade 20. As shown, the cutting blade sides 22 and 24 are inclined relative to the attachment ends 12, 14 and are offset slightly lower than the center line of the attachment ends 12, 14. This enables the cutting blade 20 when bent in the configuration shown in FIG. 4B to take the shape as illustrated. The cutting blade sides 22, 24 extend widthwise a distance $W_T$ of approximately 10.5 mm in this exemplary embodiment to form a large oval with a flat top.

Figure 4C:
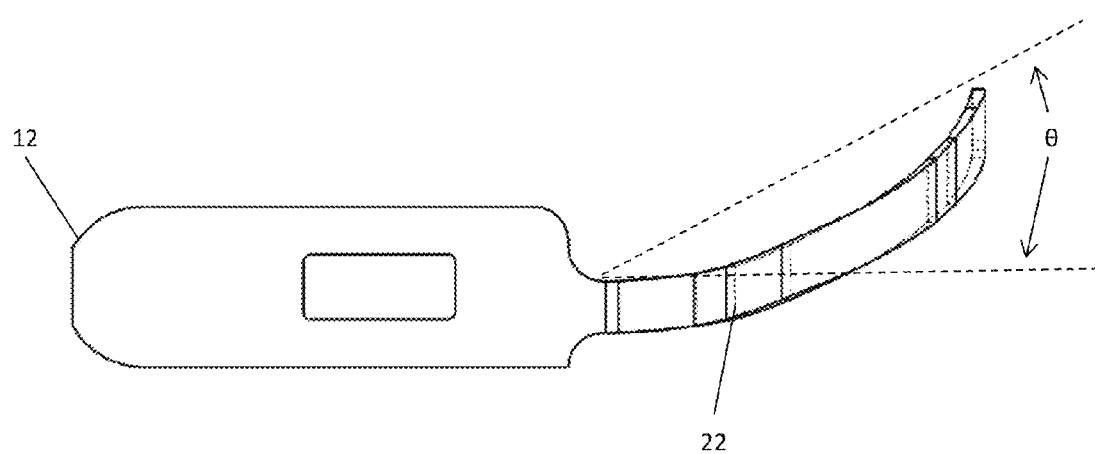
FIG. 4C is a partial view taken along lines A-A of FIG. 4B showing one portion of the cutting blade, the opposite portion having been removed.

As illustrated in FIG. 4C, the blade side portion 22 on the attachment end 12 is shown, the other side of the cutting blade 20 has the end portion 24 and 14 (not illustrated) similarly inclined. An acute angle is shown of approximately θ relative to a horizontal plane which can be varied dependent on the length and the amount of height required. However, it is believed important that the angle θ be less than 45 degrees preferably less than 30 degrees as illustrated.

Figure 4D:
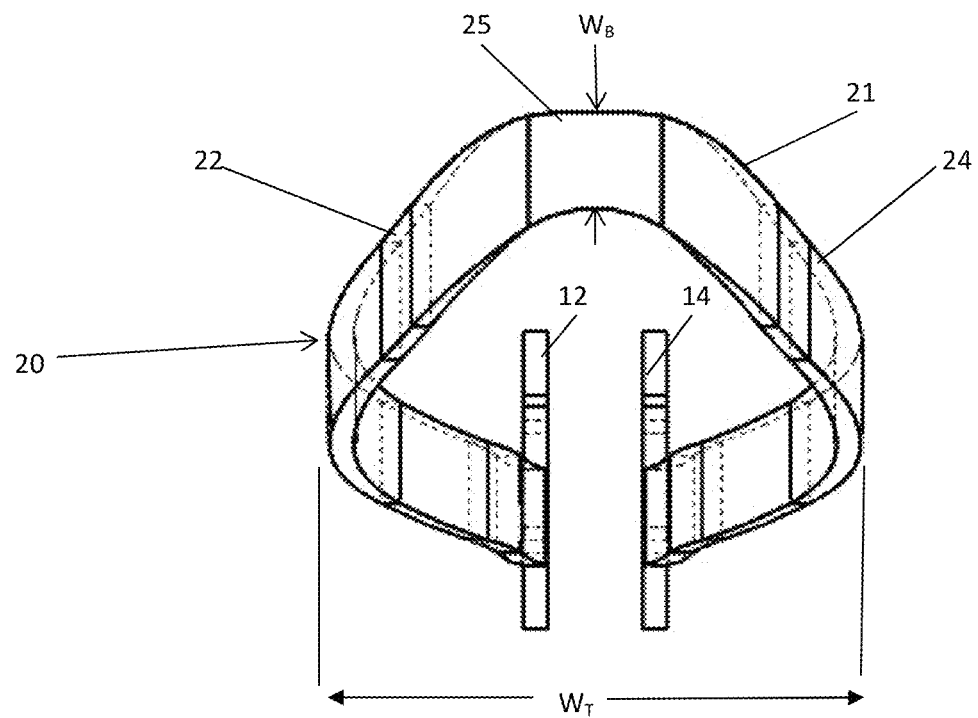
FIG. 4D is an end view of the cutting blade illustrating the vertical elevation of the cutting blade relative to the attachment portions.
Figure 5:
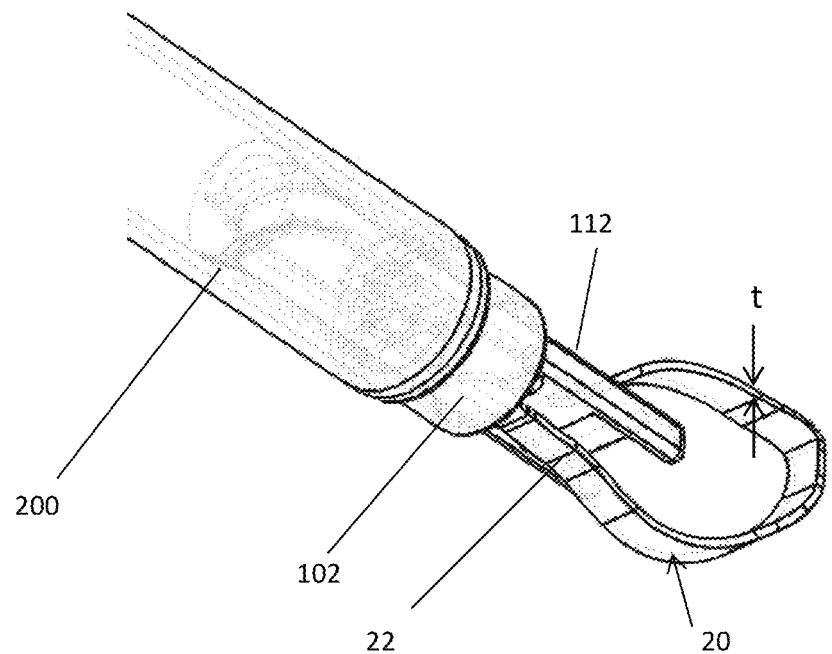
FIG. 5 is a perspective view showing the cutting blade protracted and extending outward from the tooling tube.

With reference to FIG. 4D, the cutting blade portion 20 has the sides 24 and 22 shown inclined to the flat portion 25 inclined and raised upward relative to the attachment ends 12, 14 to the flat portion 25. Again, as previously mentioned, the width of the cutting blade 20 is of substantially uniform thickness $W_B$ of about 2 mm and has a cutting edge that is also generally uniform in thickness of 0.5 mm or less. This provides a substantially strong and yet flexible blade 20 such that it can be retracted and pulled inside the tube 102. This attachment of the vertical cutter 10 is illustrated in FIG. 5 where the thickness of the blade 20 is illustrated as dimension t. In the exemplary vertical cutter 10, t was about 0.5 mm.

Figure 6:
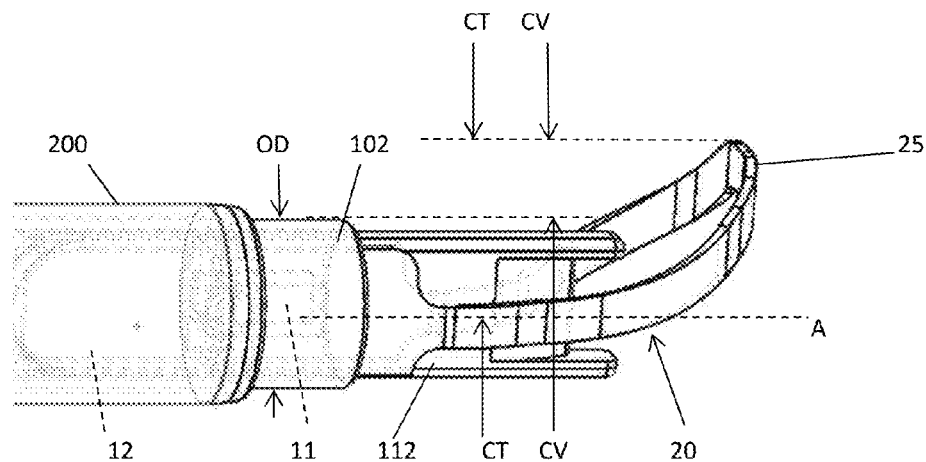
FIG. 6 is a side perspective view showing the cutting blade protracted relative to the tooling tube.

With reference to FIG. 6, the vertical cutter 10 is also shown in the protracted position where it is free of the tool tube 102. The tool tube 102 has an outside diameter OD of approximately 8 mm in this exemplary embodiment with an inside diameter of 6.85 mm. The width of the attachment ends 12, 14 is slightly less than the 6.85 mm such that they can slide inwardly to be attached to the shaft 112 at the attachment locations 114. The vertical cutter 10, when attached, has a vertical distance from the axis of rotation, this is called the cutting travel distance CT or cutting travel from the axis and it approximately 7.3 mm in the exemplary embodiment. This means that the cutting blade 20 extends above the outside diameter of the tool tube 102 by a distance of approximately 3.3 mm. It is important to note that this distance CV extending vertically above or below the tube 102 on an inclination, as shown, is achieved when the cutting blade 20 is free from the tube 102. As shown, the cutting blade 20 will extend vertically upward relative to the axis in such a fashion that the flat end 25 cutting edge can reach a maximum level of 7.3 mm in height to the vertebrae surface above it. This allows the cutting blade 20 to cut not only into the disc material, both the nucleus pulposus and the annulus fibrosus, but also to be able to scrape along the interior surface of the vertebral plate. The vertebral plate must be remembered to be somewhat of a saucer shape turned upside down wherein the edges conform inwardly slightly while the inner portion of the vertebral plate is raised in a flattened elevated dome shape. This is important in that the cutting blade 20 is designed to be able to scrape not only the disc material, but also the thin layers of this end plate of the vertebral body. By scraping it, microfractures occur and improved bone surface preparation can be achieved for a fusion implant device. As shown, the flat portion 25 has a width of approximately 3 mm or greater. This enables the device to be pushed and pulled into and out of the disc space without any rotational cutting. All cutting is achieved by linear action and to widen this void space required for the implant it is important to remember that one simply can grab the outer tube 200 that has been inserted into a small incision at the direct location and tilt it laterally slightly left or slightly right on a very small inclination. This allows the cutting blade 20 to move slightly laterally and continued pushing and pulling can create a void space approximately 10 to 15 mm for an implant 9 mm wide if so desired. The cutting blade 20 can be held in a slightly retracted position if lowered cutting heights are need. So on initial cutting, the cutting blade 20 can be slightly retracted and pushed and pulled to cut some material away and then continue to be pushed and pulled in a fully retracted condition due to the flexibility of the cutting blade 20, it will simply scrape along the bones outer edge removing a thin layer and also provide a good planar surface to receive the fusion implant device.

Figure 7:
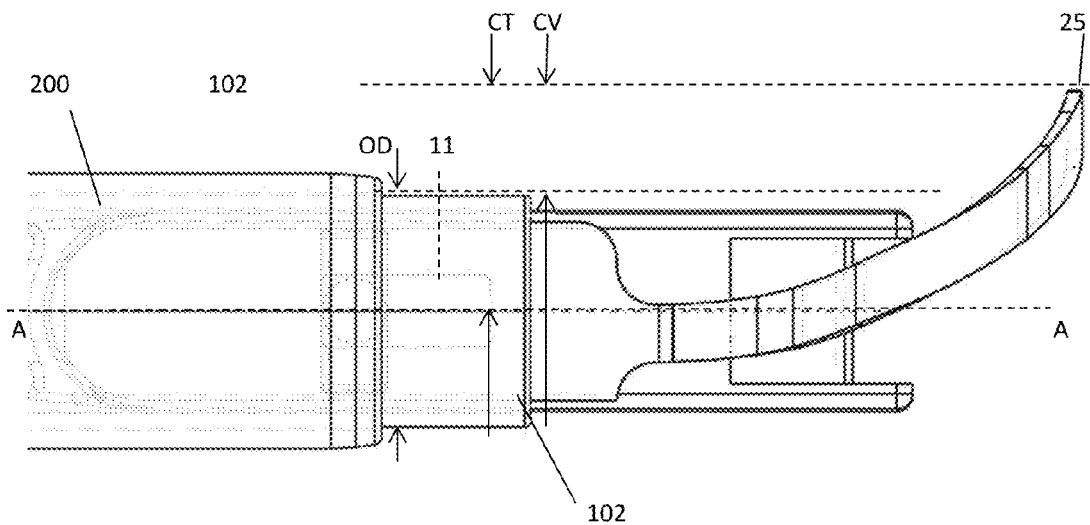
FIG. 7 is a side view showing a portion of the cutting blade with dimensions from the attachment knob to the vertical elevation above the attachment means.

FIG. 7 is a similar view to that of FIG. 6 only showing a side view and only one portion of the blade 20. It is important to note that since the cutting blade 20 is made in a looped configuration, having a somewhat oval shape flattened at the peak, it provides a substantial amount of width for cutting as the entire cutting edge 21 is on a slight incline meaning that the side surface and the top of the blade 20 form an angulation such that only the edge 21 of the cutting surface is doing the primary cutting, therefore there is no need for a very sharp razor edged blade. This blade 20 will cut at the edge 21 of the width and thickness performing a scraping action to remove both the disc material and the layers of bone material needed to be removed in preparation of the void space.

This cutting tool 100, as illustrated, with the vertical cutter 10 provides a unique way of removing disc material and preparing two adjacent vertebrae for receiving any spinal fusion implant device. The surgeon will simply locate a position on the patient's back to make an end incision. The surgeon cuts the tissue at the location by making a small incision and inserting a solid tapered dilator to allow insertion of an outer guide tube 200 that will hold the tool tube 102 portion of the tool 100. This outer tube 200 is illustrated in FIG. 7. This tube 200 is then placed into the small incision in the desired location and inserted partially therein. This tube 200 will have an outside diameter of approximately 9.2 mm when using a tool tube 102 having an outside diameter of 8 mm. This means that the outer tube 200 has an inside diameter of approximately slightly greater than 8 mm so that the tool tube 102 can slide freely in and out of this outer sheathing or guide tube 200. As illustrated, the surgeon will insert the cutting tool 100 with the retracted vertical cutter 10 inside the tool tube 102 which has been sized to pass through the inside diameter of the guide tube 200 while having the cutting blade 10 stowed internally. The surgeon will use the outer tube 200 to space the adjacent vertebral bodies wherein the disc material is intended to be removed. This spacing of the vertebrae allows the tool tube 102 to slide inward to the disc material and extending past the guide tube 200 directly towards or into the disc space. At this point the surgeon protracts the vertical cutter 10 by rotating the knob 120. As the cutting blade 20 extends past the tool tube 102 it will be moved into a free position and the shaped memory alloy cutting blade 20 will return to its free and unrestrained condition. As such the blade 20 will then extend above the inner tube by approximately 3.3 mm as discussed. When this occurs, the surgeon can then push and pull on the cutting blade 10 creating a void surface by removing the disc tissue. This includes the nucleus pulposus and the annulus fibrosus of the disc. Once this is removed the surgeon can continue to remove disc material by tilting on a slight lateral angulation, the entire guide tube 200 and tool 100 inside on a very slight angle using a lateral movement. This increases the width that can be cut such that the flat edge 25 can create a void space of at least 10 to 15 mm wide to receive the fusion implant device of 9 mm. Once this has occurred, the surgeon can continue to scrape on the exposed end plate of the vertebral body. By doing this, he or she will create cracks and fissures that will improve the osteoinductivity of the bone material adjacent the implant. This will accelerate the fusion of the bone implant and accelerate the healing time.

In order to cut the opposite adjacent vertebral body disc material, the surgeon can either retract if so desired or simply rotate the tool 100 such that it lines up with a vertical downward extension if he has previously cut in a vertical upward position. By extending the tool 100 in a downward direction he can now cut the lower vertebral body disc tissue above it and prepare that space by repeating the procedure in a push pull manner completing all the cutting without any requirement for rotational cutting of disc material. In this way, a chamber or void space that is basically rectilinear and ideally suited for receiving a spinal implant device is formed. Once all the material has been cut away and the end plates have been scraped, the device can be retracted and pulled out of the guide tube 200 such that an implant device can be positioned through the guide tube 200 to complete the procedure. While various dimensions have been mentioned for the exemplary embodiment, these dimensions can be varied using the concepts taught herein and will still be within the scope of the present invention.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A vertical cutting tool comprises:
    a shaft to which a cutting blade can be attached at one end and externally threaded at an opposite end;
    a hollow tube or cylinder for receiving the shaft internally;
    a rotatable knob affixed to the hollow tube and rotatable independent of the tube or cylinder, the knob having internal threads to engage the threads of the shaft;
    a single detachable vertical cutter having a pair of tool attachment end portions and a cutting blade extending in a loop between the attachment ends; and
    wherein the cutting blade is inclined vertically relative to a longitudinal axis of a cylinder or tube into which the attachment ends slide into, the cutting blade having a cutting edge, a portion of which when extended free of the cylinder or tube extends a distance above the tube outside diameter, the cutting edge cuts linearly relative to the longitudinal axis as the cutting blade is moved inwardly and outwardly and when positioned between adjacent vertebrae is configured to cut disc material by pushing inwardly and pulling outwardly relative to the disc as the cutting edge of the cutting blade scrapes and cuts the disc material parallel to the longitudinal axis of the cylinder or tube, and the cutting blade when retracted deflects into the cylinder or tube for insertion or extraction into or from the disc space.

2. The vertical cutting tool of claim 1 wherein the blade is cut from a flat sheet of shaped memory alloy and heat set to form the loop.

3. The vertical cutting tool of claim 2 wherein the sheet has a nominal thickness of 0.5 mm or greater.

4. The vertical cutting tool of claim 3 wherein the cutting blade has a nominal width of 2.0 mm or greater.

5. The vertical cutting tool of claim 3 wherein the cutting edges are the inclined outer edges at the intersection of the thickness and the width.

6. The vertical cutting tool of claim 1 wherein the cutting blade has curved opposite side spanning a nominal maximum between opposite sides distance of 10.5 mm or greater.

7. The vertical cutting tool of claim 6 wherein the cutting blade when withdrawn into the tube or cylinder bends or deflects the curved sides of the loop to fit the inside diameter as well as lowering or bending the flattened end vertical inclination to slide into the tube or cylinder.

8. The vertical cutting tool of claim 6 wherein the cutting blade has flattened distal end portion between the two curved sides along a vertical cutting peak extending at least 3 mm.

9. The vertical cutting tool of claim 8 wherein the cutting blade is configured to fit into a 7 mm to less than 10 mm tube or cylinder having a nominal outside diameter of 8 mm to 11 mm.

10. The vertical cutting tool of claim 9 wherein the vertical inclination extends at least 3 mm or greater above the outside diameter of the tube when the cutting blade is extended free of the tube.

11. The vertical cutting tool of claim 1 further comprises a push pull knob fixed to the rotatable knob to move the shaft to which the cutting blade is attached as the cutting blade cuts linearly inwardly and outwardly parallel to the tube or cylinder longitudinal axis.

* * * * *